United States Patent [19]

Cook et al.

[11] 4,319,043
[45] Mar. 9, 1982

[54] PROCESS FOR THE PRODUCTION OF OXYGENATED ORGANIC COMPOUNDS

[75] Inventors: John Cook; Peter M. Maitlis, both of Sheffield, England

[73] Assignees: University of Sheffield, Sheffield; BP Chemicals Limited, London, both of England

[21] Appl. No.: 133,972

[22] Filed: Mar. 26, 1980

[30] Foreign Application Priority Data

Mar. 28, 1979 [GB] United Kingdom ............ 11196/79
Jun. 14, 1979 [GB] United Kingdom ............ 20755/79

[51] Int. Cl.$^3$ .................... C07C 27/22; C07C 29/04; C07C 41/05; C07C 47/06
[52] U.S. Cl. ................................. 562/537; 562/538; 562/544; 562/548; 568/488; 568/489; 568/671; 568/902
[58] Field of Search ............ 568/902, 671, 488, 489, 568/697; 562/607, 536, 548, 539, 523, 544, 531, 606

[56] References Cited

U.S. PATENT DOCUMENTS 1,951,696 3/1934 Hofsasz ............................ 562/548
3,294,830 12/1966 Horvitz et al. .................... 568/852
3,849,459 11/1974 Maitlis et al. .

OTHER PUBLICATIONS

Fieser et al., Reagents for Organic Synthesis, vol. two, pp. 264-267 (1969).

Nesmcyanov et al., Chem. Abstracts, 1948, vol. 42, No. 12, cols. 4148i-4149c.
Maitlis, Chem. Abstracts, 1978, vol. 89, No. 11, No. 90183b.
Maitlis, Acc. Chem. Res., 1978, vol. 11, pp. 301-307.
Manchot, Annalen Der Chemie, 1920, vol. 420, pp. 170-190.

*Primary Examiner*—Nicky Chan
*Assistant Examiner*—Frederick W. Pepper
*Attorney, Agent, or Firm*—Brooks, Haidt, Haffner & Delahunty

[57] ABSTRACT

The invention relates to the production of oxygenated organic compounds comprising alcohols, aldehydes, ethers and salts of carboxylic acids. Prior art processes for the production of ethanol in particular involve the use of elevated temperatures and pressures. Milder conditions can be used in the process of the invention in which either a mercury compound of formula $(R^1OCHR^2CHR^3Hg)_nX$ (I), wherein X is an organic or inorganic anion, n is an integer equal to the valency of the anion, $R^2$ and $R^3$ are independently a hydrogen atom or an alkyl group and $R^1$ is a hydrogen atom, an alkyl group or the group —$(-CHR^2CHR^3Hg)_nX$, or the precursors of the compound (I), with a catalyst comprising a complex containing a metal of Group VIII, particularly rhodium, in the presence of a liquid reagent containing an active acidic hydrogen atom. A particularly suitable rhodium complex is one having the formula:

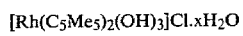

$[Rh(C_5Me_5)_2(OH)_3]Cl.xH_2O$

14 Claims, No Drawings

PROCESS FOR THE PRODUCTION OF OXYGENATED ORGANIC COMPOUNDS

The present invention relates to the production of oxygenated organic compounds comprising alcohols, aldehydes, ethers and salts of carboxylic acids.

Oxygenated organic compounds such as alcohols, and ethers are valuable industrial products. Of these compounds ethanol is produced in particularly large quantities, generally either by fermentation of natural products, eg molasses or by hydration of ethylene in the presence of an acid catalyst such as phosphoric acid supported on silica. For kinetic reasons the hydration process is generally operated at elevated temperature (typically 200° to 300° C.) and elevated pressure (typically about 60 to 70 atmospheres) although thermodynamically, ethanol formation is favoured by the use of lower temperatures. A desirable objective would be to provide a process for producing ethanol under milder conditions than those used hitherto for the hydration of ethylene.

Accordingly the present invention provides a process for the production of oxygenated organic compounds comprising alcohols, aldehydes, ethers and salts of carboxylic acids which process comprises contacting either:

(i) a mercury compound having the formula:

$$(R^1OCHR^2CHR^3Hg)_nX \qquad (I)$$

wherein X is an organic or inorganic anion, n is an integer having a value equal to the valency of the anion, $R^2$ and $R^3$ are independently a hydrogen atom or an alkyl group, and $R^1$ is a hydrogen atom, an alkyl group or the group $(-CHR^2CHR^3Hg)_nX$, or (ii) the precursors of a mercury compound having the formula (I), with a catalyst comprising a complex containing a metal of Group VIII of the Periodic Table according to Mendeleef in the presence of a liquid reagent containing an active acidic hydrogen atom under conditions of temperature and pressure which result in the formation of oxygenated organic compounds.

Compounds having the formula (I) may be prepared by reacting an olefin having the formula:

$$R^2CH=CHR^3 \qquad (II)$$

wherein $R^2$ and $R^3$ are independently a hydrogen atom or an alkyl group, with a mercury compound in the presence of water or an alcohol of formula $R^4OH$, wherein $R^4$ is an alkyl group. Thus, for example, the hydroxyethyl mercury compound may be produced by reacting ethylene at atmospheric pressure and about +5° C. with an aqueous solution of Hg (OAc)$_2$ or Hg(NO$_3$)$_2$, under careful control of pH, followed by addition of chloride ion. The β-alkoxyethylmercury compound may be similarly prepared using an alcoholic solution of the mercury compound in place of the aqueous solution. Further details of the preparative procedure can be found in Ber., 1900, 33, 1340, 2692 (K. A. Hoffmann and J. Sand); Ann, 1920, 420, 170 (W. Manchot and A. Klug) and J Amer Chem Soc, 1958, 80, 4824 (F. A. Cotton and J. R. Leto).

In the formula (I) the groups $R^1$, $R^2$ and $R^3$ may be alkyl groups. Suitably the alkyl groups may contain from 1 to 12 carbon atoms, preferably from 1 to 6 carbon atoms. Examples of suitable alkyl groups include methyl, ethyl, propyl and butyl. The group X in the formula (I) is an organic or inorganic anion. Suitable inorganic anions include the nitrate, sulphate and halide, of which the chloride is preferred. Suitable organic anions include the carboxylates, such as the acetate and propionate.

The catalyst comprises a complex of a metal of Group VIII of the Periodic Table according to Mendeleef. Suitable Group VIII metals include rhodium, cobalt and ruthenium of which rhodium is preferred. Preferably the complex is soluble in water. A particularly suitable rhodium complex is one having the formula:

$$\{Rh_2(C_5Me_5)_2(OH)_3\}Cl.xH_2O \qquad (III)$$

which complex may be prepared by reacting $\{Rh_2(C_5Me_5)_2Cl_4\}$ with aqueous sodium hydroxide. The rhodium complex of formula (III) is a stable crystalline orange solid. The preparation of this complex is described in more detail in Accts Chem Res, 1978, 11, 301 (P. M. Maitlis); J Amer Chem Soc, 1969, 91, 5970 (J. W. Kang, K. Moseley and P.M. Maitlis) and J Organometallic Chem, 1971, 26, 393 (J. W. Kang and P. M. Maitlis). The molar amount of the Group VIII metal complex employed per mole of the mercury compound having the formula (I) may suitably be in the range 0.1:1 to 0.001:1.

The liquid reagent containing an active acidic hydrogen atom may be, for example, water or an alcohol. The amount of the reagent employed is not critical provided that sufficient is added for effecting the reaction.

A particular feature of the present invention is that the mercury compound of formula (I) may be added in the form of its precursors, the precursors being an olefin having the formula (II) and a soluble mercury compound.

Preferably the olefin is passed continuously into a solution of the mercury compound and the complex containing the Group VIII metal in the liquid reagent containing an active acidic hydrogen atom. During the course of the reaction the mercury compound may be chemically reduced to an inactive species. In such circumstances it may be regenerated 'in situ' or recovered and regenerated in a separate reaction before recycle.

The conditions of temperature and pressure which effect formation of oxygenated organic compounds may be varied over a wide range. Thus the temperature may be in the range 0 to 300°C., preferably 5° to 200° C. and the pressure may be subatmospheric, atmospheric or superatmospheric, of which superatmospheric pressure is preferred. The pH at which the process is conducted has a major bearing on the nature of the products formed. Thus when the compound of formula (I) is HOCH$_2$CH$_2$HgX or the olefin of formula (II) is ethylene, the liquid reagent containing an active acidic hydrogen atom is water and the pH is 7 or below acetaldehyde is formed in addition to ethanol. At pH 7 and above besides ethanol there is also formed acetate ion which is believed to arise from disproportionation/oxidation of first-formed acetaldehyde. Preferably the process is carried out at a pH in the range 8 to 12, even more preferably in the range 9 to 12. A pH greater than 7 may suitably be achieved by the addition of an alkali or alkaline earth metal oxide or hydroxide, the most suitable being sodium hydroxide.

Whether the reaction is carried out batchwise or continuously the product will be obtained as a solution in the liquid reagent. The product may be recovered from such solutions in known manner.

The nature of the product will depend on the nature of the olefin used in the preparation of the mercury compound of formula (I) or as a precursor of this compound, the alkaline material added to achieve a pH greater than 7 and also on the nature of the liquid reagent containing an active acidic hydrogen atom. Thus the product may contain an alcohol or an ether. For example when the olefin is ethylene, the reagent is water and sodium hydroxide is added to adjust the pH, ethanol and sodium acetate are formed. In the presence of ethanol as the liquid reagent diethyl ether is formed. When ethylene is replaced by propylene in the presence of water as the reagent 2-propanol is formed. The invention will now be illustrated by reference to the following Examples.

EXAMPLE 1

30 mg ($5 \times 10^{-5}$ mole) of {Rh$_2$(C$_5$Me$_5$)$_2$OH$_3$}Cl.xH$_2$O, where x=probably 4, in 2 ml of 2M aqueous NaOH was reacted with 0.013 g ($5 \times 10^{-5}$ mole) of HOCH$_2$CH$_2$HgCl dissolved in 2 ml. of 2M aqueous NaOH at ambient temperature and atmospheric pressure.

The aqueous product was analysed by Gas Chromatography (GC) to show the presence of $7 \times 10^{-6}$ mole ethanol; this was confirmed by NMR spectroscopy which also showed that the remainder, forming about 85% of the product, was sodium acetate.

EXAMPLE 2

The procedure of Example 1 was repeated except that the amount of HOCH$_2$CH$_2$HgCl was increased to $10 \times 10^{-5}$ mole, the amount of ethanol produced was $2 \times 10^{-5}$ mole, the remainder of the product being sodium acetate (~85%).

EXAMPLE 3

The procedure of Example 1 was repeated except that the amount of HOCH$_2$CH$_2$HgCl was increased to $5 \times 10^{-4}$ mole. The amount of ethanol produced was $8 \times 10^{-5}$ mole, the remainder of the product being sodium acetate (~85%).

EXAMPLE 4

The procedure of Example 1 was repeated except that the amount of HOCH$_2$CH$_2$HgCl was increased to $1.8 \times 10^{-3}$ mole. The amount of ethanol produced was $3 \times 10^{-4}$ mole, the remainder of the product being sodium acetate (~85%).

In Examples 1 to 4 there is an approximately linear relationship between the amount of ethanol produced and the amount of HOCH$_2$CH$_2$HgCl used. Furthermore approximately 0.15 to 0.2 mole of ethanol were obtained per mole of HOCH$_2$CH$_2$HgCl. The catalytic nature of the rhodium complex is demonstrated by the small amount used ($5 \times 10^{-5}$ mole).

EXAMPLE 5

Ethylene (1atm) was bubbled into a solution of 0.025 g ($4 \times 10^{-5}$ mole) of complex (III) and 0.0132 g Hg(OAc)$_2$ ($4 \times 10^{-5}$ mole) in 2 ml H$_2$O at 20° C. 2 ml of 2M aqueous NaOH was then added. Analysis by gas chromatography showed the presence of $5.3 \times 10^{-6}$ mole of ethanol.

EXAMPLE 6

The procedure of Example 5 was repeated except that the amount of Hg(OAc)$_2$ was increased to $2.0 \times 10^{-4}$ mole. The amount of ethanol produced was $3.4 \times 10^{-5}$ mole.

EXAMPLE 7

The procedure of Example 5 was repeated except that the amount of Hg(OAc)$_2$ was increased to $3.9 \times 10^{-4}$ mole. The amount of ethanol was $6.0 \times 10^{-5}$ mole.

EXAMPLE 8

The procedure of Example 5 was repeated except that the amount of Hg(OAc)$_2$ was increased to $9.8 \times 10^{-4}$ mole. The amount of ethanol produced was $1.5 \times 10^{-4}$ mole.

There is again, in Example 5–8, an approximately linear relationship between the amount of mercury salt used and the amount of ethanol produced and in each case between 0.13 and 0.15 mole of ethanol were formed per mole of Hg(OAc). Again the rhodium complex is present in catalytic amount.

We claim:

1. A process for the production of a product comprising an alkanol which process comprises contacting either (i) a mercury compound having the formula:

$$(R^1OCHR^2CHR^3Hg)_nX \qquad (I)$$

wherein X is an organic or inorganic anion, n is an integer having a value equal to the valency of the anion, R$^2$ and R$^3$ are independently a hydrogen atom or an alkyl group and R$^1$ is a hydrogen atom, or (ii) the precursors of a mercury compound having the formula I, which precursors are an olefin of the formula R$^2$CH=CHR$^3$, and a soluble mercury compound with an effective amount of a catalyst comprising a complex of a metal of Group VIII of the Periodic Table according to Mendeleef in the presence of water at a temperature of from 0+ to 300° C.

2. A process according to claim 1 wherein a precursor is used, the olefin is ethylene, sodium hydroxide is added to adjust the pH in the range of 8 to 12 and the product contains ethanol and sodium acetate.

3. A process according to claim 1 wherein the pH is 7 or less, and the product contains an aldehyde and an alcohol.

4. A process according to claim 1 wherein a precursor is used, the olefin is ethylene, the pH is controlled to 7 or less, and the product contains ethanol and acetaldehyde.

5. A process for the production of a product comprising a dialkyl ether which process comprises contacting either (i) a mercury compound having the formula:

$$(R^1OCHR^2CHR^3Hg)_nX \qquad (I)$$

wherein X is an organic or inorganic anion, n is an integer having a value equal to the valency of the anion, R$^2$ and R$^3$ are independently a hydrogen atom or an alkyl group and R$^1$ is an alkyl group or the group (—CHR$^2$CHR$^3$Hg)$_n$X, or (ii) the precursors of a mercury compound having the formula I, which precursors are an olefin of the formula R²CH=CHR³, and a soluble mercury compound.
with an effective amount of a catalyst comprising a complex of a metal of Group VIII of the Periodic Table according to Mendeleef in the presence of an alkanol at a temperature of from 0° to 300° C.

6. A process according to claim 5 wherein a precursor is used, and the olefin is ethylene, sodium hydroxide is added to adjust the pH in the range 8 to 12 and the product contains diethyl ether and sodium acetate.

7. A process according to claim 1 or 5 wherein in the formula (I) R¹, R² and R³ are alkyl groups containing from 1 to 12 carbon atoms.

8. A process according to claim 1 wherein the alkyl groups contain from 1 to 6 carbon atoms.

9. A process according to claim 1 or 5 wherein the anion is nitrate, sulphate, chloride, acetate or propionate.

10. A process according to claim 1 or 5 wherein the metal of Group VIII of the Periodic Table is rhodium, cobalt or ruthenium.

11. A process according to claim 10 wherein the metal of Group VIII is rhodium.

12. A process according to claim 1 or 5 wherein the catalyst is a rhodium complex of formula:

$$\{Rh_2(C_5Me_5)_2(OH)_3\} Cl.x H_2O \qquad (III)$$

13. A process according to claim 1 or 5 wherein the molar amount of the Group VIII metal complex employed per mole of the mercury compound having the formula (I) is in the range 0.1:1 to 0.001:1.

14. A process according to claim 1 or 5 wherein the pH is in the range 8 to 12.

* * * * *

UNITED STATES PATENT AND TRADEMARK OFFICE
CERTIFICATE OF CORRECTION

PATENT NO. : 4,319,043
DATED : 3/9/82
INVENTOR(S) : JOHN COOK and PETER M. MAITLIS It is certified that error appears in the above—identified patent and that said Letters Patent is hereby corrected as shown below:

Col. 4, line 23, "Hg(OAc)" should read -- $Hg(OAc)_2$ --.

Col. 4, line 45, "0+" should read --0°--

Col. 5, claim 8, line 19, after "claim 1" insert --or 5--

Signed and Sealed this

Nineteenth Day of April 1983

[SEAL]

Attest:

GERALD J. MOSSINGHOFF

Attesting Officer     Commissioner of Patents and Trademarks